United States Patent [19]

Schouteeten et al.

[11] 4,346,238
[45] Aug. 24, 1982

[54] PROCESS FOR THE PREPARATION OF CRYSTALLINE SODIUM PARAFORMYLPHENOLATE

[75] Inventors: Alain Schouteeten, Ezanville; Yani Christidis, Paris, both of France

[73] Assignee: Societe Francaise Hoechst, France

[21] Appl. No.: 147,678

[22] Filed: May 7, 1980

[30] Foreign Application Priority Data

May 14, 1979 [FR] France ................... 79 12173

[51] Int. Cl.$^3$ ..................... C07C 45/54; C07C 47/565
[52] U.S. Cl. .................................. 568/432; 568/435; 568/442
[58] Field of Search ............... 568/431, 435, 442, 432, 568/438

[56] References Cited

U.S. PATENT DOCUMENTS 2,062,206  11/1936  Boedecker .
3,673,257   6/1972  Di Bella .
4,163,759   8/1979  Bauer et al. ...................... 568/435

FOREIGN PATENT DOCUMENTS 514871   7/1955  Canada .............................. 568/442
751687   6/1933  France .
2132364  11/1972 France .

OTHER PUBLICATIONS

Istvan Simonyi et al., Magyar Kém. Folyoirat, vol. 62 (1956) pp. 76–79.

Satpathy et al., Jour. Indian Chem. Soc., vol. 49 (1972) 615–620.

Primary Examiner—Bernard Helfin
Attorney, Agent, or Firm—Karl W. Flocks and Associates

[57] ABSTRACT

Sodium paraformylphenolate crystallized with two molecules of water is manufactured by:
(a) condensing glyoxylic acid with an excess of phenol in water in the presence of sodium hydroxide at a temperature comprised between 30° C. and 100° C.;
(b) neutralizing the solution thus obtained and then freeing it from the unconverted phenol by steam distillation or extraction with a water-immiscible organic solvent and then subjecting it hot under a pressure of oxygen, to a catalytic decarboxylating oxidizing degradation in the presence of sodium hydroxide;
(c) allowing the aqueous solution so-obtained, after removal of the catalyst by filtration, and then concentration hot under vacuum to 60% plus or minus 10% of its initial volume, to crystallize; and
(d) draining the precipitated crystals, washing them and then drying them to constant weight under vacuum of 1 mm of mercury at 20° C., to obtain sodium paraformylphenolate crystallized with 2 molecules of water or dried to constant weight under a vacuum of 1 mm of mercury at 100° C. to obtain it in anhydrous form. The product is useful for preparing parahydroxy benzaldehyde quantitatively and without other purification reactions.

9 Claims, No Drawings

PROCESS FOR THE PREPARATION OF CRYSTALLINE SODIUM PARAFORMYLPHENOLATE

BACKGROUND OF THE INVENTION

1. Field of the Invention

The present invention relates to crystalline sodium paraformylphenolate, to the process for its industrial production from glyoxylic acid and to its use.

It relates in particular, by way of novel industrial product, to sodium paraformylphenolate crystallised with two molecules of water.

2. Description of the Prior Art

In the Prior Art, sodium paraformylphenolate is a derivative of parahydroxybenzaldehyde widely used, either to obtain parahydroxybenzaldehyde, or to prepare various paraalkoxybenzaldehydes, or lastly to carry out various condensations involving the aldehydic carbonyl group.

However, in these reactions, sodium paraformylphenolate is only an intermediate not isolated in the pure crystalline state.

To Applicant's knowledge, it was isolated intermediately by ISTVAN SIMONYI and Coll., Magyar Kém. Folyoirat 62, 76–9 (1956). These authors prepared and recrystallised this product in water before converting it into parahydroxybenzaldehyde by 20% of sulfuric acid in water, but they neither determined its physical characteristics, nor obtained this product crystallised with two molecules of water, in the pure state enabling recourse to the subsequent purification steps of the resulting parahydroxybenzaldehyde to be dispensed with.

In the same way, it is to be noted that sodium paraformylphenolate has never been isolated in the pure crystalline state with two molecules of water, although it is abundantly used, particularly in aqueous solution. In solution in the latter solvent, L. A. COHEN, J. Org. Chem. 22, 1333–5 (1957) determined its ultraviolet absorption spectrum: max 330 nm $\log\epsilon = 3.9$.

K. K. SATPATHY and Coll., J. Indian Chem. Soc. 49, 615–20 (1972) investigated the behaviour of 3-nitro 4-chloro benzaldehyde with respect to dry sodium paraformylphenolate obtained by treating pure parahydroxybenzaldehyde with the stoichiometric amount of sodium ethylate in ethanol, then by filtering it, and drying to constant weight at 100°–110° C., the precipitate obtained; but no physical constant was given.

GENERAL DESCRIPTION OF THE INVENTION

It has now been discovered that it is possible, starting from phenol and from glyoxylic acid in a sodium aqueous medium, to obtain sodium paraformylphenolate crystallised with two molecules of water, which accordingly constitutes the first aspect of the present invention.

According to another aspect of the invention, there is provided a process which, without isolating the intermediate product and using the same reaction medium, consists, in a first step, of condensing glyoxylic acid in aqueous solution with an excess of phenol in water in the presence of sodium hydroxide; then of subjecting, in a second step, the preceding aqueous solution neutralised and freed of unconverted phenol either by steam distillation, or by extraction with a water-immiscible organic solvent, to a catalytic oxidising decarboxylating degradation in a sodium alkaline medium; in a third step, isolating the sodium paraformylphenolate crystallised with 2 molecules of water, after removal of the catalyst by filtration; followed by concentration hot of the filtrate and draining and drying, at 20° C. under vacuum, the crystalline precipitate obtained by leaving this concentrated aqueous solution at ambient temperature.

More precisely, this process consists of condensing between 30° C. and 100° C., advantageously between 70° C. and 85° C., under an inert atmosphere, 1 mole of 50% glyoxylic acid in water with 2 to 3 moles of phenol in about 2 liters of water containing 2 to 3 moles of sodium hydroxide during 30 to 70 minutes, neutralising the solution thus obtained at pH = 6.5 ± 0.3 with 50% sulfuric acid in water, then extracting the unconverted phenol with 1,2-dichloro ethane, then subjecting the aqueous solution alkalinised with 3 to 4 moles of sodium hydroxide to catalytic decarboxylating oxidising degradation at a temperature $\leq 140°$ C. and at an oxygen pressure $\leq 6$ bars in the presence of cupric sulfate alone or admixed with other salts of noble metals of Group VIII of the MENDELEIEV Table for 0.1 to 5 hours, concentrating the filtered aqueous suspension while hot to 60% ± 10% of its initial weight and lastly draining and then drying to constant weight under vacuum at 20° C., in the presence of potassium hydroxide pellets, the crystalline precipitate formed by leaving this concentrate at ambient temperature for some hours.

Sodium paraformylphenolate crystallised with 2 molecules of water thus obtained, is in the form of hygroscopic colorless platelets having a momentary melting point of 122° ± 3° C. with decomposition. Its analysis shows that it is pure and that it contains two molecules of water of crystallisation. According to the drying conditions, it loses its water of crystallisation more or less completely. Sodium paraformylphenolate crystallised with 2 molecules of water, does not lose its water of crystallisation when it is dried at 20° C. to constant weight under vacuum of 1 mm of mercury in the presence of potassium hydroxide pellets. On the other hand, under the same conditions, but at 100° C., anhydrous sodium paraformylphenolate is obtained which is in the form of very hygroscopic, slightly yellow platelets, which become colorless by the absorption of water, and having a melting point > 250° C.

Sodium paraformylphenolate crystallised with 2 molecules of water has an aqueous solubility at 20° C. of 0.0916 mole in 100 g of water. Contrary to the prior art, acidification at pH = 1 of such an aqueous solution provides quantitatively pure crystalline parahydroxybenzaldehyde, of melting point 116°–117° C., without other purification operations, which proves the interest of the product according to the invention.

It may however by pointed out that, according to a preferred process, to avoid on the one hand the possible presence of corrosive or slightly water soluble sodium salts such as sodium chloride or sodium sulfate and on the other hand, a loss of parahydroxybenzaldehyde due to the fact of its slight aqueous solubility: 0.0113 mole in 100 g of water at 30.5 C, it is preferred to carry out this conversion hot with the stoichiometric amount of acetic acid in solution in about 10 volumes of water. In this way after filtration of the aqueous suspension obtained, cooled to 5° C. and drying under vacuum to constant weight at 60° C., crystalline pure parahydroxybenzaldehyde can be obtained, having a melting point of 116°–117° C., with a yield of 100% of the theoretical calculated with respect to the sodium paraformylphenolate utilised.

According to another aspect of the invention there is provided a process for the industrial manufacture of paraanisaldehyde comprising using sodium paraformylphenolate crystallised with two molecules of water for this purpose.

Paraanisaldehyde is an essential oil very much used in perfumery. Its use in sophisticated formulations, requires a very pure aroma, and in particular, the absence of any by-product even at concentrations of the order of ppm which would change its odor.

It is known to produce paraanisaldehyde by methylation of the phenolic hydroxyl group of parahydroxybenzaldehyde either by means of methyl iodide according to F. TIEMANN & collaborators, Ber. 10, 63 (1877), or by trimethylphenylammonium hydroxide according to W. M. RODIONOW & Col. Arch. Pharm. 266, 119 (1928), or by methyl paratoluenesulfonate according to S. J. KANEWSKAJA, Arch. Pharm. 271, 466 (1933), or lastly by dimethyl sulfate according to V. AVRAMENKO & Coll., Khim.-Farm. Zh., 2, 18-10 (1968) and French patent 2,321,472 or by a modification in the presence of an aprotic polar solvant such as dimethylformamide according to M. PAILLER & Coll., Monatsch. Chem. 99, 103 (1968).

It has now been discovered that one can obtain paraanisaldehyde with a substantially quantitative yield by methylating with dimethyl sulfate in slight excess, sodium paraformylphenolate crystallised with 2 molecules of water, in a water immiscible organic solvent. Thus, the fact of having available sodium paraformylphenolate crystallised with two molecules of water, permits its methylation in an organic solvent without the use of alkaline agents and in particular, the use of non-polar aromatic solvents such as benzene or toluene which are industrially economical and which are known as being little favorable to the O-alkylation of phenols.

According to the invention, sodium paraformylphenolate crystallised with 2 molecules of water, is suspended with stirring in about 3 volumes of toluene, then treated towards 60° C. for some hours with a slight excess ≦20% of dimethyl sulfate; the suspension is then diluted with about 2 volumes of water, decanted and the organic phase freed of toluene by evaporation under vacuum is subjected to stripping under vacuum. In this way paraanisaldehyde is isolated in the form of a colorless liquid with a yield greater than 95% of the theoretical calculated with respect to the sodium paraformylphenolate utilised.

According to a preferred operational method, the crude wet, undried recrystallised sodium paraformylphenolate is supended in about 3 volumes of toluene. This suspension is then heated under reflux until the removal by azeotropic distillation of about one half of the water present, then the suspension cooled to 60° C. is treated with stirring with a slight excess ≦20% of dimethyl sulfate introduced drop by drop in about one hour; the heating and stirring are continued then for 2 to 3 hours, before diluting this suspension with about 2 volumes of water.

After decantation, washing with toluene of the separated aqueous phase, then washing with water the combined organic phases, the oily residue obtained after removal of the toluene by evaporation under vacuum of the organic phase is stripped under vacuum. In this way liquid paranisaldehyde is isolated, having a boiling point under 30 mm of mercury of 138°-141° C. with a yield greater than 95% of theory calculated with respect to the sodium paraformylphenolate utilised.

DESCRIPTION OF PREFERRED EMBODIMENTS

The following examples are given by way of illustration and are to be considered as in no way limiting the invention.

EXAMPLE 1

A solution of 296 g (2 moles) of 50% glyoxylic acid in water, 564 g (6 moles) of phenol and 160 g (4 moles) of soda in pellets in 3.6 liters of water are heated for 30 minutes at 82° C., with stirring and in a nitrogen atmosphere. After cooling to 40° C., the reaction solution is brought to pH 6.5 with 50% aqueous sulfuric acid, then after cooling to ambient temperature, the unconverted phenol is extracted with 1,2-dichloroethane; 376 g (4 moles) of phenol are thus isolated after removal of the solvent. The aqueous solution alkalinized with 8 moles of sodium hydroxide is heated for 5 hours at 120° C. under a pressure of 4 bars of oxygen in the presence of 3.5 g of cupric sulfate pentahydrate. After cooling and placing at ambient pressure, the filtered suspension obtained is concentrated to about 55% of its initial weight under vacuum at a temperature below 85° C., then left for some hours to crystallise at ambient temperature. The crystallised precipitate is then drained, washed with water by forming a paste and dried at 20° C. under vacuum of 1 mm of mercury to constant weight in the presence of potassium hydroxide pellets. In this way 216.16 g (1.2 mole) of sodium paraformylphenolate crystallised with 2 molecules of water was isolated in colorless platelets, having a melting point of 122°±3° C. with decomposition, namely a yield of 60% with respect to the glyoxylic acid utilised. This product can be recrystallised hot and cold in 0.75 volumes of water with a yield of 60% for the first crop. The melting point was not changed.

| Micro-analysis: very hygroscopic product. | | | | | |
|---|---|---|---|---|---|
| | | C % | H % | H$_2$O %** | Ash* |
| C$_7$H$_5$O$_2$Na, 2H$_2$O | Calculated | 46,67 | 5,03 | 20,0 | 39,43 |
| MW = 180,14 | Found | 46,4 | 5,1 | 20,2 | 38,9 |

*Sulphuric ash
**determined by loss in the oven at 100° C.

Solubility in 100 g of water at 20° C.: 0.0916 mole
  Physical analyses:

| NMR of the proton in deuterated DMSO (internal TMS reference) | | | |
|---|---|---|---|
| S = 9.12 ppm | singlet | 1H | H (CHO) |
| S = 6.65 ppm | multiplet | 4H | aromatic |

VPC (carried out on the free phenol obtained by acidification) absence of an ortho isomer

EXAMPLE 2

Procedure was as in Example 1 but the decarboxylating oxidising degradation was carried out at 110° C. under an oxygen pressure of 6 bars for 4 hours. In this way sodium paraformylphenolate crystallised with 2 molecules of water was isolated, having a melting point of 122°±3° C. with a yield of 57.6% with respect to the glyoxylic acid utilised.

EXAMPLE 3

Procedure was as in Example 1 but the decarboxylizing oxidising degradation was carried out in 3 hours in the presence of 3 g of cupric sulphate, pentahydrate and of 3 g of ferric chloride. In this way sodium paraformylphenolate crystallised with 2 molecules of water, having a melting point of 122°±3° C. was obtained with a yield of 56.2% with respect to the glyoxylic acid utilised.

EXAMPLE 4

Procedure is as in Example 3 but as the decarboxylating oxidising degradation catalyst, 3 g of cupric sulphate pentahydrate and 3 g of cobalt acetate tetrahydrate is used. In this way sodium paraformylphenolate crystallised with 2 molecules of water is isolated with a yield of 60% with respect to the glyoxylic acid utilised.

EXAMPLE 5

A solution of 296 g (2 moles) of 50% glyoxylic acid in water, 564 g (6 moles) of phenol and 160 g (4 moles) of soda pellets in 3.6 liters of water, are heated for 30 minutes at 100° C., with stirring and in a nitrogen atmosphere. Procedure is then as in Example 1. In this way sodium paraformylphenolate crystallised with 2 molecules of water having a melting point of 122°±3° C. is isolated, with a yield of 56.47% with respect to the glyoxylic acid used.

EXAMPLE 6

A 50% solution in water of 296 g (2 moles) of glyoxylic acid, 564 g (6 moles) of phenol and 200 g (5 moles) of soda in pellets in 3.6 liters of water, are heated for 1 hour at 50° C., with stirring and in a nitrogen atmosphere. Then procedure is as in Example 1.

In this way sodium paraformylphenolate crystallised with 2 molecules of water having a melting point of 122°±3° C. is isolated with a yield of 61.2% with respect to the glyoxylic acid utilised.

EXAMPLE 7

A 50% solution in water of 296 g (2 moles) of glyoxylic acid, 564 g (6 moles) of phenol and 180 g (4.5 moles) of pelletized soda in 3.6 liters of water is heated for 30 minutes from 30° to 85° C., then cooled in 30 minutes to 40° C., with stirring and in a nitrogen atmosphere. Then procedure is as in Example 1.

In this way sodium paraformylphenolate crystallised with 2 molecules of water having a melting point of 122°±3° C., is isolated with a yield of 63.5% with respect to the glyoxylic acid utilised.

EXAMPLE 8

A 50% solution in water of 296 g (2 moles) of glyoxylic acid, 564 g (6 moles) of phenol and 160 g (4 moles) of soda in pellets in 3.6 liters of water are heated for 30 minutes to 70° C. Procedure is then as in Example 1. In this way sodium paraformylphenolate crystallised with 2 molecules of water, having a melting point of 122°±3° C., is isolated with a yield of 65.5% with respect to the glyoxylic acid utilised.

EXAMPLE 9

0.225 mole (40.53 g) of sodium paraformylphenolate crystallised with 2 molecules of water is treated with 150 g of an aqueous solution containing 0.225 mole of acetic acid. This suspension is heated to 80° C., and then the solution was cooled to 5°±2° C. for some hours. The crystalline precipitate thus obtained is drained, washed with water then dried to constant weight under 30 mm of mercury at 60° C. In this way 0.225 mole (27.4 g) of crystalline parahydroxybenzaldehyde having a melting point of 116°–117° C. is isolated, namely a quantitative yield of the theory calculated with respect to the sodium paraformylphenolate utilised.

| Microanalysis | | C % | H % |
|---|---|---|---|
| $C_7H_6O_2$ | Calculated | 68.84 | 4.95 |
| MW = 122.12 | Found | 68.6 | 4.7 |

EXAMPLE 10

A suspension with stirring of 2 moles (360 g) of sodium paraformylphenolate crystallised with 2 molecules of water in 3 volumes of toluene is treated at 60° C.±3° C. with 2.4 moles (302.7 g) of dimethyl sulphate introduced slowly in about one hour. The heating is pursued to 60° C. and the stirring continued for 150 minutes more after the end of the introduction, and then the hot reaction medium is diluted with 450 cm³ of water. The cooled suspension obtained is decanted, the aqueous phase is washed with toluene, and the combined organic phases are washed with water, dried, filtered, and finally concentrated under vacuum at 60° C. to remove the toluene. The oily residue obtained is stripped under a vacuum of 30 mm of mercury. In this way 1.94 mole (264.11 g) of paraanisaldehyde in the form of a colorless oil distilling under 30 mm of mercury at 138°–141° C. is collected, namely a yield of 97% of theory calculated with respect to the sodium paraformylphenolate utilised.

| Microanalysis | | C % | H % |
|---|---|---|---|
| $C_8H_8O_2$ | Calculated | 70.58 | 5.92 |
| MW = 136.13 | Found | 70.8 | 6.0 |

Functional group evaluation: —CHO (NH₂OH, HCl): 99.8±1%

EXAMPLE 11

576 g of sodium paraformylphenolate crystallised with 2 molecules of water, undried containing 38% of water (namely 1.98 mole of sodium paraformylphenolate crystallised with 2 molecules of water and 219 g of water of hydration) was heated under reflux in 3 volumes of toluene with azeotropic distillation of the water. After having collected 120 g of water in the distillate, the temperature of the reaction medium was lowered to 60° C. and 265 g (2.1 moles) of dimethyl sulfate was added with stirring in about one hour: then the heating was continued at 60° C. and the stirring for 150 minutes after the end of the introduction. The suspension obtained was then treated as in the Example 9. In this way after distillation 261 g (1.92 mole) of paraanisaldehyde was isolated having a boiling point under 30 mm of mercury of 138°–141° C., namely a yield 97% of theory calculated with respect to the sodium paraformylphenolate applied.

It is self-evident that the present invention has only been described purely by way of explanation and that this description is in no way limiting and that any useful modification could be introduced therein without departing from its scope as defined by the appended claims.

We claim:

1. Process for manufacturing crystalline sodium paraformylphenolate comprising:
   (a) condensing glyoxylic acid with an excess of phenol in water in the presence of sodium hydroxide at a temperature comprised between 30° C. and 100° C.;
   (b) neutralising the solution thus obtained and then freeing it from the unconverted phenol by steam distillation or by extraction with a water-immiscible organic solvent, and then subjecting it hot under a pressure of oxygen, to a catalytic decarboxylating oxidising degradation in the presence of sodium hydroxide;
   (c) allowing the aqueous solution so-obtained, after removal of the catalyst by filtration, and then concentration hot under vacuum to 60% plus or minus 10% of its initial volume, to crystallise; and
   (d) draining the precipitated crystals, washing them and then drying them to constant weight under vacuum of 1 mm of mercury at about 20° C. to obtain sodium paraformylphenolate crystallised with two molecules of water.

2. Process according to claim 1, wherein the condensation of the glyoxylic acid with the phenol is stirred out at a temperature comprised between 70° C. and 85° C.

3. Process according to claim 1, in which the condensation is carried out with one mole of glyoxylic acid in aqueous solution and an excess of 2 to 3 moles of phenol.

4. Process according to claim 1, in which one mole of glyoxylic acid in aqueous solution is condensed with an excess of phenol in the presence of 2 to 3 moles of sodium hydroxide.

5. Process according to claim 1, in which the decarboxylating oxidising degradation is carried out at a temperature comprised between 90° C. and 140° C.

6. Process according to claim 1, in which the decarboxylating oxidising degradation is carried out under an oxygen pressure less than or equal to 6 bars.

7. Process according to claim 1, in which the decarboxylating oxidising degradation is carried out in the presence of 2 to 6 moles of sodium hydroxide relative to the glyoxylic acid utilised.

8. Process according to claim 1, in which the decarboxylating oxidising degradation is carried out in the presence of cupric salts.

9. Process according to claim 1, in which the decarboxylating oxidising degradation is carried out in the presence of cupric salts and salts selected from those of metals of group VIII of the MENDELEIEV Table.

* * * * *